(12) United States Patent
Sakai et al.

(10) Patent No.: US 7,138,142 B2
(45) Date of Patent: Nov. 21, 2006

(54) PROCESS FOR PRODUCING GRANULES CONTAINING BRANCHED AMINO ACIDS

(75) Inventors: Hidetoshi Sakai, Kawasaki (JP); Mitsuyasu Ida, Kawasaki (JP); Chisato Makino, Kawasaki (JP); Tomoaki Kawano, Kawasaki (JP); Akira Yabuki, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 10/897,000

(22) Filed: Jul. 23, 2004

(65) Prior Publication Data

US 2005/0003015 A1 Jan. 6, 2005

Related U.S. Application Data

(63) Continuation of application No. PCT/JP03/00578, filed on Jan. 23, 2003.

(30) Foreign Application Priority Data

Jan. 24, 2002 (JP) ............................. 2002-015003

(51) Int. Cl.
*A61K 9/14* (2006.01)
*A61K 9/50* (2006.01)

(52) U.S. Cl. ...................... 424/489; 424/499

(58) Field of Classification Search ............... 424/489, 424/499
See application file for complete search history.

(56) References Cited

U.S. PATENT DOCUMENTS

| | | | |
|---|---|---|---|
| 3,764,703 A * | 10/1973 | Bergstrom et al. | 514/419 |
| 4,499,076 A | 2/1985 | Ohashi et al. | |
| 4,753,804 A * | 6/1988 | Iaccheri et al. | 424/491 |
| 5,635,198 A * | 6/1997 | Nishimura et al. | 424/438 |
| 5,776,491 A | 7/1998 | Allen, Jr. et al. | |
| 5,935,635 A * | 8/1999 | Mori et al. | 426/656 |
| 6,499,984 B1 * | 12/2002 | Ghebre-Sellassie et al. | 425/135 |
| 6,733,781 B1 * | 5/2004 | Abu-Izza et al. | |

FOREIGN PATENT DOCUMENTS

| | | |
|---|---|---|
| EP | 1 334 722 | 8/2003 |
| JP | 3-22366 | 1/1982 |
| JP | 7-73480 | 8/1986 |
| JP | 3-204814 | 9/1991 |
| JP | 03-211824 B1 | 9/1991 |
| JP | 3-259731 | 11/1991 |
| JP | 7-25838 | 1/1995 |
| JP | 8-198748 | 8/1996 |
| JP | 2001-258509 | 9/2001 |
| JP | 3-259731 | 2/2002 |
| JP | 3259731 | 2/2002 |
| WO | 02/49638 A1 | 6/2002 |
| WO | WO 02/49638 | 6/2002 |

OTHER PUBLICATIONS

Pharmaceutical product interview form relating to BCAA preparation LIVACT granules, "branched chain amino acid preparation of LIVACT granules", revised Jul. 1996 (rev. ed. 2).
Dictionary of Unit, rev. 4th ed., Maruzen, pp. 299-300; section of "mesh".
Pharmaceutics, rev. 2nd ed., Nankodo, pp. 106-115; section of "granules".

* cited by examiner

*Primary Examiner*—Humera N. Sheikh
(74) *Attorney, Agent, or Firm*—Oblon, Spivak, McClelland, Maier & Neustadt, P.C.

(57) ABSTRACT

The problem of the present invention is to provide pharmaceutical granules containing, as active amino acid ingredients, three kinds of branched chain amino acids of isoleucine, leucine and valine, which has a smaller specific volume than conventional products, and a production method thereof. As a result of intensive studies, granules containing, as active amino acid ingredients, three kinds of branched chain amino acids of isoleucine, leucine and valine and a production method thereof have been provided, which are characterized by adding an acid to a particle mixture of three kinds of branched chain amino acids of isoleucine, leucine and valine and granulating the mixture, which has solved the above-mentioned problem.

20 Claims, No Drawings

PROCESS FOR PRODUCING GRANULES CONTAINING BRANCHED AMINO ACIDS

CONTINUING APPLICATION DATA

The present application is a continuation of International application No. PCT/JP03/00578, filed Jan. 23, 2003, which claims benefit to Japanese patent application No. 15003/2002 filed Jan. 24, 2002, which is incorporated herein by reference.

TECHNICAL FIELD

The present invention relates to pharmaceutical granules containing three kinds of branched chain amino acids of isoleucine, leucine and valine as active amino acid ingredients, and a production method thereof.

BACKGROUND ART

A pharmaceutical preparation containing three kinds of branched chain amino acids of isoleucine, leucine and valine as active ingredients is an effective therapeutic agent for liver diseases. These three kinds of branched chain amino acids have a strong bitter taste and unique amino acid smell and require large amounts for one dose. For production of a preparation, therefore, the problems of reduction of bitter taste and smell, a small-volume of a dose and the like should be solved.

In particular, when a solid preparation contains particles of these three kinds of branched chain amino acids, the preparation is required to have uniform contents of these three kinds of branched chain amino acids per dose. However, when this requirement is to be met by reducing the size of starting material amino acid particles as in the case of conventional solid preparations, the volume thereof in one dose increases, which in turn makes the preparation bulky and difficult to swallow during administration.

In the case of granules, for example, the active ingredient is mostly pulverized to not more than 50 μm before use, thereby to satisfy the requirements of ensured content uniformity, improvement in solubility and the like. The granules produced in this way generally show a specific volume of 2.0 mL/g or above, though subject to slight change depending on the type of granulation method, granulation conditions and the like. In the case of the aforementioned three kinds of branched chain amino acid particles, a single dose of the branched chain amino acids is about 4–5 g. Therefore, when a granule preparation is produced by pulverizing them to not more than 50 μm, its volume becomes about 8–10 mL and takes up much space in the mouth, making it extremely difficult to swallow.

DISCLOSURE OF THE INVENTION

It is therefore a problem of the present invention to provide a granule containing, as active ingredients, three kinds of branched chain amino acids of isoleucine, leucine and valine, which has a smaller specific volume than conventional products, and a production method thereof.

In an attempt to solve the above-mentioned problems, the present inventors have conducted intensive studies and found that, in the case of the aforementioned three kinds of branched chain amino acids, addition of an acid to a granulation starting material in a granulation step increases the solubility of the active ingredients to tighten the granule, based on which a method of making a granule containing branched chain amino acids, which has a smaller specific volume than conventional products, has been found. In addition, the present inventors have found that, by controlling the particle size of the branched chain amino acids to be granulation starting materials, a branched chain amino acid-containing granule having a still smaller specific volume can be granulated. The present invention encompasses the following respective inventions.

(1) A method of making a granule comprising three kinds of branched chain amino acids of isoleucine, leucine and valine, as active ingredients, which comprises adding an acid to a particle mixture of three kinds of branched chain amino acids of isoleucine, leucine and valine, and granulating the mixture.

(2) The method of (1), wherein the acid is at least one selected from the group consisting of citric acid, malic acid, tartaric acid, acetic acid, carbonic acid, phosphoric acid and hydrochloric acid.

(3) The method of (1) or (2), wherein the particle mixture comprises three kinds of branched chain amino acids, having a particle size of 10–1000 μm, and wherein the mixture is granulated as a starting material.

(4) The method of (1) or (2), wherein the particle mixture comprises three kinds of branched chain amino acids, having a particle size of 100 μm–800 μm, and wherein the mixture is granulated as a starting material.

(5) The method of (1) or (2), wherein the particle mixture comprises three kinds of branched chain amino acids, having a particle size of 150 μm–500 μm, and wherein the mixture is granulated as a starting material.

(6) The method of any of (1) to (5), wherein the granule has a specific volume of 1.93-1.59 mL/g.

(7) The method of any of (1) to (6), wherein the isoleucine, leucine and valine have a mass ratio of isoleucine/leucine/valine=1/1.9-2.2/1.1-1.3.

(8) The method of any of (1) to (7), wherein the granule is produced by a high-shear granulation method, an extrusion granulation method, a fluidized bed granulation method, a dry compressing granulation method or a tumbling granulation method.

(9) A granule comprising, as active ingredients, three kinds of branched chain amino acids of isoleucine, leucine and valine, and produced by the method of any of the aforementioned (1)–(8).

(10) A granule, a powder, a pill, a tablet, a troche or a capsule produced using the granule of the aforementioned (9).

In the present invention, the "granule" includes granules and powders, as well as granules used for producing tablets, troches or capsules.

In the granule of the present invention, as isoleucine, which is one of the active ingredients, particles conventionally produced by fermentation methods and having a particle size of not more than 1 mm, which meets the standard of the Japanese Pharmacopoeia, the US Pharmacopoeia or the European Pharmacopoeia, is used, but isoleucine is not limited thereto.

As leucine, a particle conventionally produced by fermentation methods or extraction methods and having a particle size of not more than 1 mm, which meets the standard of the Japanese Pharmacopoeia, the US Pharmacopoeia or the European Pharmacopoeia, is used, but leucine is not limited thereto.

As valine, a particle conventionally produced by fermentation methods or synthetic methods and having a particle size of not more than 1 mm, which meets the standard of the Japanese Pharmacopoeia, the US Pharmacopoeia or the European Pharmacopoeia, is used, but valine is not limited thereto.

As method for controlling the size of particles of the three kinds of branched chain amino acids of isoleucine, leucine and valine, which are subjected to granulation, is not particularly limited and general grinding method is employed. As the grinders usable for pulverization, impact (high-speed roll) mills such as a hammer mill etc., tumbler (media) mills such as ball mill etc., fluidized (air jet) mills such as jet mill etc., and the like can be mentioned.

In the granule of the present invention, the mixing ratio of the three kinds of branched chain amino acids of isoleucine, leucine and valine is isoleucine/leucine/valine=1/1.9-2.2/1.1-1.3 in a mass ratio.

As the acid usable for granulation may be any as long as it can be added as a pharmaceutical product. From the aspect of flavor, preferred are tartaric acid, citric acid, malic acid, ascorbic acid and acetic acid from organic acids, and hydrochloric acid, carbonic acid and phosphoric acid from inorganic acids. The amount of the acid to be added is free of any particular limitation, and it is appropriately added generally in the range of 0.1–5% by mass of the starting material mixture. The acid may be solely added to an amino acid mixture in the form of an aqueous solution, or may be added along with other additives such as a binder.

For the production of the granule preparation of the present invention, a binder can be used. As the binder, any substance can be used without any particular limitation as long as it is usable for pharmaceutical purposes, such as cellulose derivatives such as methyl cellulose, hydroxypropyl cellulose, hydroxypropylmethyl cellulose, hydroxypropylmethyl cellulose phthalate and the like, starches such as corn starch, wheat starch and the like, synthetic polymers such as polyvinylpyrrolidone, acrylic acid polymer and the like, natural polymers such as gum arabic, gelatin and the like, and the like. The amount of use thereof may be any as long as general granulation is attainable.

For the production of the granule preparation of the present invention, flavoring agents such as sweetening agents (e.g., saccharin sodium, aspartame etc.), odor improving agents (e.g., menthol, lemon flavor etc.), and the like, which are of the kinds generally employed, can be added.

The granule containing the aforementioned three kinds of amino acid particles in the pharmaceutical granule preparation of the present invention can be produced using any instrument, such as a high-shear granulator, an extrusion granulator, a fluidized bed granulator, a dry compaction granulator, a tumbling granulator and the like, with reference given to a high-shear granulator.

The high-shear granulation method comprises charging or spray water or a binder solution on a powder, followed by shearing-tumbling-compacting by the rotation of a stirring blade to achieve granulation. For this method, a vertical horizontal high-shear granulator is used.

The extrusion granulation method comprises extruding a plasticized powder from a screen with a number of holes to achieve granulation. For this method, a front extruding granulator, a disc pelleter granulator, a ring die granulator, a basket granulator, an oscillating granulator, a cylinder granulator and the like are used.

The fluidized bed granulation method comprises spraying water or a binder solution while flowing a powder to allow coagulation of the powder. For this granulation method, a fluidized bed granulator, a high-shear fluidized bed granulator, a tumbling fluidized bed granulator or a high-shear tumbling fluidized bed granulator is used.

The dry compression granulation method comprises compressing a powder for formation without using water or a binder solution. For this method, a roll press, a briquetting machine, a single action tableting machine or a rotary tableting machine is used. The tumbling granulation method comprises granulation by rolling a powder, and for this method, a drum granulator, a disc granulator, a vibration granulator or a rotating disk granulator is used.

The granule of the present invention can be coated for the purpose of masking a bitter taste and the like.

BEST MODE FOR EMBODYING THE INVENTION

Specific examples of the present invention are shown in the following as working examples, which are not to be construed as limitative.

In each Example, the particle size of the branched chain amino acid (starting material) was measured by the following method.

Using a laser diffraction/scattering particle size distribution analyzer (manufactured by Horiba, Ltd., LA-920), an appropriate amount of 2-propanol is placed in a circulation tank and circulated with stirring and ultrasonication, after which blank measurement is done (ultrasonication is turned off while measurement). Then, an appropriate amount of 2-propanol is placed in the circulation tank and amino acids for measurement is added such that transmittance becomes about 85%. The mixture is circulated with stirring and ultrasonication, the ultrasonication is stopped, and the particle size is measured. For an average particle size, a median size was used.

EXAMPLE 1

Three kinds of branched chain amino acids (weight ratio, leucine:isoleucine:valine=2:1:1.2), 2.3 kg, pulverized in advance was mixed to give a branched chain amino acid mixture having a median size of 22 μm.

Thereto was added a binding solution having a composition shown in Table 1, and the mixture was granulated in a high-shear granulator (high speed mixer FS-10, manufactured by Fukae Powtec Co., Ltd.; agitator 300 rpm, chopper 3600 rpm, 15 min). The obtained wet granulated product was dried in a flow coater FLO-5 (manufactured by Freund Corporation) at a charge air temperature of 80° C. to give a dry granule. The granules had a specific volume of 1.88 mL/g.

TABLE 1

| component | amount |
| --- | --- |
| povidone | 23.2 g |
| polyvinyl alcohol | 19.1 g |
| tartaric acid | 23.1 g |
| saccharin sodium | 9.9 g |
| purified water | 750 g |
| total | 825.4 g |

EXAMPLE 2

Three kinds of branched chain amino acids (weight ratio, leucine:isoleucine:valine=2:1:1.2, 2.3 kg) pulverized in advance in the same manner as in Example 1 was mixed to give a branched chain amino acid mixture having a median size of 22 μm.

Thereto was added a binding solution having a composition shown in Table 2, and the mixture was granulated in a high-shear granulator (high speed mixer FS-10, manufactured by Fukae Powtec Co., Ltd.; agitator 300 rpm, chopper 3600 rpm, 15 min). The obtained wet granulated product was dried in a flow coater FLO-5 (manufactured by Freund Corporation) at a charge air temperature of 80° C. to give a dry granule. The granules had a specific volume of 1.93 mL/g.

TABLE 2

| component | amount |
| --- | --- |
| povidone | 23.2 g |
| polyvinyl alcohol | 19.1 g |
| citric acid | 23.2 g |
| saccharin sodium | 9.9 g |
| purified water | 850 g |
| total | 925.4 g |

COMPARATIVE EXAMPLE 1

Three kinds of branched chain amino acids (weight ratio, leucine:isoleucine:valine=2:1:1.2, 2.3 kg) pulverized in advance in the same manner as in Example 1 was mixed to give a branched chain amino acid mixture having a median size of 22 μm.

Thereto was added a binding solution having a composition shown in Table 3, and the mixture was granulated in a high-shear granulator (high speed mixer FS-10, manufactured by Fukae Powtec Co., Ltd.; agitator 300 rpm, chopper 3600 rpm, 15 min). The obtained wet granulated product was dried in a flow coater FLO-5 (manufactured by Freund Corporation) at a charge air temperature of 80° C. to give a dry granule. The granules had a specific volume of 1.99 mL/g.

TABLE 3

| component | amount |
| --- | --- |
| povidone | 23.2 g |
| polyvinyl alcohol | 19.1 g |
| saccharin sodium | 9.9 g |
| purified water | 850 g |
| total | 902.2 g |

EXAMPLE 3

Three kinds of branched chain amino acids (weight ratio, leucine:isoleucine:valine=2:1:1.2, 2.3 kg) was mixed and ground in a pin mill (sample mill manufactured by NARA MACHINERY CO., LTD.) using a 3 mmφ screen to give a branched chain amino acid ground mixture having a median size of 219 μm.

Thereto was added a binding solution having a composition shown in Table 4, and the mixture was granulated in a high-shear granulator (high speed mixer FS-10, manufactured by Fukae Powtec Co., Ltd.; agitator 300 rpm, chopper 3600 rpm, 15 min). The obtained wet granulated product was dried in a flow coater FLO-5 (manufactured by Freund Corporation) to give dry granules. The granules had a specific volume of 1.59 mL/g.

TABLE 4

| component | amount |
| --- | --- |
| povidone | 23.2 g |
| polyvinyl alcohol | 19.1 g |
| tartaric acid | 11.6 g |
| saccharin sodium | 9.9 g |
| purified water | 330.0 g |
| total | 393.8 g |

INDUSTRIAL APPLICABILITY

The branched chain amino acid-containing granule produced by the present invention has a smaller specific volume than conventional products. Thus, a dose per administration can be made smaller, which provides a great effect of improving administrability.

The invention claimed is:

1. A method of making a granule comprising three kinds of branched chain amino acids of isoleucine, leucine and valine, as active ingredients, which comprises adding an acid to a particle mixture of three kinds of branched chain amino acids of isoleucine, leucine and valine, and granulating the mixture, by a high-shear granulation method, wherein the isoleucine, leucine and valine have a mass ratio of isoleucine/leucine/valine=1/1.9 to 2.2/1.1 to 1.3.

2. The method of claim 1, wherein the acid is at least one selected from the group consisting of citric acid, malic acid, tartaric acid, acetic acid, carbonic acid, phosphoric acid and hydrochloric acid.

3. The method of claim 1, wherein the particle mixture comprises three kinds of branched chain amino acids, having a particle size of 10–1000 μm, and wherein the mixture is granulated as a starting material.

4. The method of claim 1, wherein the particle mixture comprises three kinds of branched chain amino acids, having a particle size of 100 μm–800 μm, and wherein the mixture is granulated as a starting material.

5. The method of claim 1, wherein the particle mixture comprises three kinds of branched chain amino acids, having a particle size of 150 μm–500 m, and wherein the mixture is granulated as a starting material.

6. The method of claim 1, wherein the granule has a specific volume of 1.93–1.59 mL/g.

7. A granule comprising, as active ingredients, three kinds of branched chain amino acids of isoleucine, leucine and valine, and produced by the method of claim 1.

8. The method of claim 2, wherein the particle mixture comprises three kinds of branched chain amino acids, having a particle size of 10–1000 μm, and wherein the mixture is granulated as a starting material.

9. The method of claim 2, wherein the particle mixture comprises three kinds of branched chain amino acids, having a particle size of 100 μm–800 m, and wherein the mixture is granulated as a starting material.

10. The method of claim 2, wherein the particle mixture comprises three kinds of branched chain amino acids, having a particle size of 150 μm–500 m, and wherein the mixture is granulated as a starting material.

11. The method of claim 2, wherein the granule has a specific volume of 1.93–1.59 mL/g.

12. The method of claim 3, wherein the granule has a specific volume of 1.93–1.59 mL/g.

13. A granule comprising, as active ingredients, three kinds of branched chain amino acids of isoleucine, leucine and valine, and produced by the method of claim 2.

14. A granule comprising, as active ingredients, three kinds of branched chain amino acids of isoleucine, leucine and valine, and produced by the method of claim 3.

15. A granule comprising, as active ingredients, three kinds of branched chain amino acids of isoleucine, leucine and valine, and produced by the method of claim 4.

16. A granule comprising, as active ingredients, three kinds of branched chain amino acids of isoleucine, leucine and valine, and produced by the method of claim 5.

17. A granule comprising, as active ingredients, three kinds of branched chain amino acids of isoleucine, leucine and valine, and produced by the method of claim 6.

18. A granule comprising, as active ingredients, three kinds of branched chain amino acids of isoleucine, leucine and valine, and produced by the method of claim 8.

19. A granule comprising, as active ingredients, three kinds of branched chain amino acids of isoleucine, leucine and valine, and produced by the method of claim 9.

20. A granule comprising, as active ingredients, three kinds of branched chain amino acids of isoleucine, leucine and valine, and produced by the method of claim 10.

* * * * *

UNITED STATES PATENT AND TRADEMARK OFFICE
CERTIFICATE OF CORRECTION

| | | |
|---|---|---|
| PATENT NO. | : 7,138,142 B2 | Page 1 of 1 |
| APPLICATION NO. | : 10/897000 | |
| DATED | : November 21, 2006 | |
| INVENTOR(S) | : Hidetoshi Sakai et al. | |

It is certified that error appears in the above-identified patent and that said Letters Patent is hereby corrected as shown below:

Col. 6

Claim 5, line 49, "150 μm-500 m" should read --150 μm-500 μm--.

Claim 9, line 62, "100 μm-800 m" should read --100 μm-800 μm--.

Claim 10, line 66, "150 μm-500 m" should read --150 μm-500 μm--.

Signed and Sealed this
Fourth Day of October, 2011

David J. Kappos
*Director of the United States Patent and Trademark Office*